United States Patent
Cheng

(10) Patent No.: US 10,479,774 B2
(45) Date of Patent: *Nov. 19, 2019

(54) **METHOD FOR SEPARATING FLAVONOID SUBSTANCES IN *CAMELLIA NITIDISSIMA* CHI BASED ON A MAGNETIC NANOPARTICLES-PAMAM NANO COMPOSITES**

(71) Applicant: Shenzhen Violin Technology Co.,Ltd., Shenzhen (CN)

(72) Inventor: Jinsheng Cheng, Meizhou (CN)

(73) Assignee: Shenzhen Violin Technology Co., Ltd., Shenzhen (CN)

( * ) Notice: Subject to any disclaimer, the term of this patent is extended or adjusted under 35 U.S.C. 154(b) by 790 days.

This patent is subject to a terminal disclaimer.

(21) Appl. No.: 14/938,855

(22) Filed: Nov. 12, 2015

(65) Prior Publication Data

US 2016/0137623 A1    May 19, 2016

(30) Foreign Application Priority Data

Nov. 13, 2014 (CN) .......................... 2014 1 0639271

(51) Int. Cl.
  *C07D 311/24*   (2006.01)
(52) U.S. Cl.
  CPC .................. *C07D 311/24* (2013.01)
(58) Field of Classification Search
  None
  See application file for complete search history.

(56) References Cited

U.S. PATENT DOCUMENTS

2016/0136224 A1*  5/2016  Cheng .................... A61K 36/82
                                                 424/729

OTHER PUBLICATIONS

Johnson, Separation of flavonoid compounds in Sephadex LH-20, 1968, J Chromatography, 33: 539-541 (Year: 1968).*

* cited by examiner

*Primary Examiner* — Terry A McKelvey
*Assistant Examiner* — Catheryne Chen
(74) *Attorney, Agent, or Firm* — Wayne & Ken, LLC; Tony Hom

(57) ABSTRACT

The present invention discloses a method for separating flavonoid substances in *Camellia nitidissima* Chi based on a magnetic nanoparticles-PAMAM nano composites, which comprises the following steps: preparing PAMAM dendrimer, then using the PAMAM dendrimer to prepare the magnetic nanoparticles-PAMAM nano composites, then adding the obtained magnetic nanoparticles-PAMAM nano composites in a *Camellia nitidissima* Chi extract, extracting and performing magnetic separation on the flavonoid substances in *Camellia nitidissima* Chi under ultrasound or microwave condition. According to the present invention, flavonoid substances with faintly acid characteristics are extracted and adsorbed in a plant concentrate such as *Camellia nitidissima* Chi or *Hedyotis diffusa* etc. based on the magnetic nanoparticles-PAMAM nano composites, in a successive step, high efficiency separation of the flavonoid substances can be realized by the technologies such as magnetic separation and microwave-assisted extraction.

3 Claims, 2 Drawing Sheets

METHOD FOR SEPARATING FLAVONOID SUBSTANCES IN *CAMELLIA NITIDISSIMA* CHI BASED ON A MAGNETIC NANOPARTICLES-PAMAM NANO COMPOSITES

CROSS-REFERENCE TO RELATED APPLICATIONS

This application is a continuation in part of, and claims priority to, Chinese Patent Application No. 201410639271.1 with a filing date of Nov. 13, 2014. The content of the aforementioned application, including any intervening amendments thereto, is incorporated herein by reference.

TECHNICAL FIELD

The present invention refers to the field of biotechnology, more particularly, to a method for separating flavonoid substances in *Camellia nitidissima* Chi based on a magnetic nanoparticles-PAMAM nano composites.

BACKGROUND OF THE PRESENT INVENTION

*Camellia nitidissima* Chi (or name *Camellia nitidissima*) is a precious and rare plant in the world, which is as famous as *Cathaya argyrophylla, Alsophila spinulosa, Davidia involucrate* and other precious living plant fossils. Founded in 1993 by Chinese botanist Jinglie Zuo in Fangcheng of Guangxi Province, *Camellia nitidissima* Chi is one of eight national first-class protective plants and included in plant species in Annex II of *Convention on International Trade in Endangered Species of Wild Fauna and Flora*. At present, 40 breeds and 5 variants of *Camellia nitidissima* Chi are well known to the world, mainly distributed in Vietnam and southern edge of subtropical zone and northern edge of tropical zone within the borders of Guangxi Province in China.

*Camellia nitidissima* Chi, Inula nervosa Wall, Noni Puree, Yeast β-glucan, and Tissue culture of *Saussurea involucrata* are new resources food approved by the No. 9 document in 2010 of Ministry of Health of China. The leaves and flowers of *Camellia nitidissima* Chi are enriched in total flavones (isoflavonoids, biflavonoids, anthocyanin and neoflavonoids etc.), tea polyphenols, multiple amino acids and microelement etc. by studies.

As one kind of compounds widely existed in the nature, flavonoids are the derivative of chromane, characterized in that it is with basic framework of C6-C3-C6. Flavonoids can be divided into dozens of categories: flavones, flavanols, isoflavones, flavanones, flavanonols, aurones, flavanones, anthocyanidins, chalcones and chromones etc., over 4000 kinds of flavonoids are found at present, mainly existed in the leaves, fruits, roots and skin of plants, experimental results show it is of extensive physiological and pharmacological activity (including antioxidant, scavenging oxygen free radicals, antivirus, anticancer, anti-inflammatory, anti-aging etc.), so the study on flavonoids has become a hot topic in Chinese and foreign medical profession. Traditional extracting methods mainly include ultrafiltration, enzymolysis, adsorption by coarse pored resin, supercritical fluid extraction, ultrasonic method and microwave field extraction etc. (Rui Zhang, Yaqin Yu, Yang Shi. *Study on Flavonoids Extracting Technology. Food and Machinery*, 2003, 01, 21-22), while they are always restricted by extracting efficiency or cost.

At present, most studies on active ingredients of flavonoid substances in *Camellia nitidissima* Chi are confined to traditional ultraviolet and chromatographic detection or solvent extraction, membrane separation etc., like Zhihua Zhan performed qualitative analysis on the chemical component in leaves of *Camellia nitidissima* Chi. The flavonoids in *Camellia nitidissima* Chi are occupied about 2.33% by qualitative analysis. (Zhihua Zhan, *Extraction and Separation of Flavones in Leaves of Camellia nitidissima Chi*[D], Guangxi Normal University, 2006); repeated silica gel column chromatography, Sephadex LH 20 gel chromatography, ODS chromatography and repeated recrystallization and other methods are adopted by Xiao Peng and co-workers to perform separation and purification on chemical component in flowers of *Camellia nitidissima* Chi, and the structure is identified on the basis of physicochemical constants and spectrum analysis. 13 compounds including flavonoids are obtained from the separation of ethanol extract in flowers of *Camellia nitidissima* Chi. (Xiao Peng, Dayong Yu, Baomin Feng, Ling Tang, Yongqi Wang, Liying Shi. *Study on Chemical Component in Flowers of Camellia nitidissima Chi*. Guangxi Plant, 2011, 31(04), 550-553). The content of total saponins, total polyphenol (tannin) and total flavones in different plant parts of *Camellia nitidissima* Chi, *Camellia pubipetala, Camellia impressinervis, Camellia chrysantha* and *Camellia chrysanthoides* is detected through ultraviolet spectrophotometry by Qian Tang. The content of total saponins, total polyphenol(tannin) and total flavones of alcohol extract in flowers of *Camellia nitidissima* Chi is respectively 21.30%, 6.56% and 21.76%. (Qian Tang, Yanying Luo, Yongqi Wang etc. *Quantitative Analysis on Chemical Component of Camellia nitidissima Chi Section*, Lishizhen Med Mater Med Res, 2009, 20(4), 769-771); while Quanbin Chen and co-workers take following method, the leaves of *Camellia nitidissima* Chi are used as the material to extract flavones, high purification aglycone is obtained by hydrolyzing the flavones, solvent extraction, column chromatography and other methods; structure characterization is performed by melting point, TLC, liquid chromatography, infrared spectroscopy, nuclear magnetic resonance method and other analysis methods to confirm the leaves of *Camellia nitidissima* Chi contain flavonoid glycosides, the aglycon of which is quercetin and kaempferol. (Quanbin Chen, Zhihua Zhan, Qiaoyun Zhang, Na Liao. *Separation and Purification of Flavones Aglucone in Leaves of Camellia nitidissima Chi and Characterization*. Guangxi Tropical Agriculture, 2005, 6, 10-11).

Flavonoids in *Hedyotis diffusa* are extracted by microwave-assisted technology by Caixia Zhang and co-workers, and the extraction processes are optimized, the primary and secondary sequence of affecting flavones extraction ratio is as follows on the basis of identification of chemical structure of extract, extracting temperature, ethanol concentration, extracting time and solid to liquid ratio, the best extraction process is ethanol concentration 80%, extraction time of 40 min, solid to liquid ratio of 1:100 under 40° C., the extraction ratio of flavones in *Hedyotis diffusa* reaches to 2.86% under this condition. (Caixia Zhang, Dingjian Cai, Wenying Fang. *Optimization of Flavones Extracting Process and Structure Identification*. Anhui Agricultural Sciences, 2011, 39(01), 131-133); Jialin Li and co-workers discussed the effect of extraction temperature, extraction time, solid to liquid ratio and ethanol concentration on the total flavones extraction ratio of *Rhus chinensis*. The extraction ratio is the best under extraction time of 10 min, extraction temperature of 60° C., solid to liquid ratio of 1:60 and ethanol concentration of 70%. Experimental results show the extraction ratio of total flavones reaches to 6.65% under the best conditions. (Jialin Li, Suzhen Wu, Zhanyu Bei. *Study on Extraction Process of Total Flavones in Rhus Chinensis*).

Dendrimer is a new class of three-dimensional and highly ordered macromolecules in recent years. PAMAM is one of the most widely and deeply studied dendrimer, with highly branched and highly symmetrical structure and a large number functional groups on the surface and other unique structural features, PAMAM is widely used in drug carrier, surface active agent, catalyst, nano materials, membrane materials and other fields. One generation of obtained product will be increased every time the structural unit of dendrimer is repeated and multiplied, at present, 10.0G divergent method is the leading and most mature synthetic method in the synthesis of PAMAM dendrimer, this method is of mild reaction condition, rapid reaction and high selectivity. (Huimin Tan, Yunjun Luo. *Dendritic Polymer* [M]. Beijing: Chemistry Industry Press, 2001).

PAMAM dendrimer is of rich amine terminated structure and inner secondary amine and quaternary amine structure, so PAMAM dendrimer presents faintly alkalinity. With phenolic hydroxyl group, most flavonoids present faintly acidity, it is easy to be dissolved into water containing soda, and it can be precipitated out after acidification. The first reason is the acidity of flavone phenolic hydroxyl group, and the second is the ring opening of mother nucleus of flavone under alkaline conditions, so 2'-hydroxychalcone is formed, with the rise of polarity, it is dissolved. (Xuefeng Guo, Yongde Yue. *Research Progress of Extraction, Separation and Purification of Flavonoids and Content Measuring Method. Anhui Agricultural Sciences*, 2007, 35(26), 8083-8086). According to the present invention, the high efficiency separation of the flavonoid substances in *Camellia nitidissima* Chi is realized by the extraction and adsorption effect of PAMAM dendrimer with faintly alkalinity and flavonoid substances with faintly acidity.

For better separation of the flavonoid substances adsorbed by PAMAM, the magnetic nanoparticles-PAMAM nano composites of the present invention are prepared by compounding PAMAM and magnetic nanoparticles, like ferrites ($Fe_3O_4$, $\gamma$-$Fe_2O_3$ and $MeFe_2O_4$, wherein Me=Co, Ni, Mn), Fe, Co, Ni, alloy particles and iron nitrides (FeN, $Fe_2N$, $\varepsilon$-$Fe_3N$ and $Fe_{16}N_2$) and other particles, separating the magnetic nanoparticles-PAMAM nano composites extracted and adsorbed with faintly acidity flavonoid substances from extract by magnetic effect; and finally performing separation on the adsorbed flavonoid substances with magnetic nanoparticles-PAMAM nano composites by ultrasound-assisted extraction.

SUMMARY OF THE PRESENT INVENTION

The purpose of the present invention is to solve problems above mentioned by offering a method for separating flavonoid substance in *Camellia nitidissima* Chi based on a magnetic nanoparticles-PAMAM nano composites.

To achieve purpose, the present invention employs the following technical solution:

A method for separating flavonoid substances in *Camellia nitidissima* Chi based on the magnetic nanoparticles-PAMAM nano composites, which comprises the following steps:

1) Preparing PAMAM Dendrimer

Ethylenediamine is used as the centronucleus to prepare PAMAM dendrimer, the first step is performing Michael addition reaction between ethylenediamine and methyacrylate to obtain generation 0.5 polyamidoamine dendrimer, namely PAMAM G0.5, the reaction has high selectivity under 25° C.; the second step is reacting the obtained PAMAM G0.5 with excessive ethylenediamine under 25° C. to obtain generation 1.0 polyamidoamine dendrimer, namely PAMAM G1.0; one generation will be increased every time above two steps reaction are repeated, PAMAM of different generations are obtained by constantly repeating above two steps under proper conditions.

2) Preparing the Magnetic Nanoparticles-PAMAM Nano Composites

The magnetic nanoparticles are dispersed into methanol through magnetic separation to obtain solution with 0.0128 mol/L concentration; diluting 25 mL methanol solution of magnetic nanoparticles prepared above to 150 mL by methanol and ultrasonication is performed for 30 min; then adding 10 mL 3-aminopropyltriethoxysilane, the solution is stirred strongly together with ultrasonication for 7 h; performing magnetic separation on the obtained solution after washing it by methanol for 5 times, then the solution is dispersed in methanol to obtain 5 wt % solution for standby.

50 mL 5 wt % magnetic nanoparticles methanol solution is used as the initial solution, adding 200 mL methanol solution with methyacrylate, the volume concentration of the methyacrylate is 20%, performing ultrasonication to the mixture for 7 h in water bath at room temperature; then collecting magnetic nanoparticles by magnet and washing it for 5 times by methanol and performing magnetic separation; after washing, adding 40 mL methanol solution with ethylenediamine, the volume concentration of the ethylenediamine is 20%, performing ultrasonication for 3 h at room temperature; then washing the magnetic nanoparticles for 5 times with methanol and performing magnetic separation; methanol solution with methyacrylate and methanol solution with ethylenediamine are added repeatedly, higher generations of magnetic nanoparticles modified by dendrimer will be obtained for each cycle; washing the solution after cycle with 25 mL methanol for 3 times and with 25 mL water for 5 times, the magnetic nanoparticles modified by PAMAM dendrimer is collected and obtained by magnetic separation.

3) Extracting and Performing Magnetic Separation on the Flavonoid Substances in *Camellia nitidissima* Chi Adding the obtained magnetic nanoparticles-PAMAM nano composites in the *Camellia nitidissima* Chi extract, extracting 0.5-3 h under ultrasound or microwave condition, after extraction, separating the nanoparticles-PAMAM nano composites with flavonoid substances adsorbed and extracted through magnetic separation, the flavonoid substances adsorbed by magnetic nanoparticles are extracted and separated by organic solvents from separated nanoparticles-PAMAM nano composites, the nanoparticles-PAMAM nano composites can be recycled again after ablution and activation.

As a further plan of the present invention, the magnetic nanoparticles include Fe, Co, Ni as well as alloy particles, ferrites and iron nitrides; ferrites include $Fe_3O_4$, $\gamma$-$Fe_2O_3$ and $MeFe_2O_4$, wherein Me=Co, Ni, Mn; iron nitrides include FeN, $Fe_2N$, $\varepsilon$-$Fe_3N$ and $Fe_{16}N_2$.

As a further plan of the present invention, the organic solvents include ethanol, methanol, DMSO and acetone.

As a further plan of the present invention, the method also applies to plant leaves, flowers, fruits and roots enriched in flavonoid substances.

Compared with the prior art, the advantage of the present invention is that flavonoid substances with faintly acidity are extracted and adsorbed in a plant concentrate such as *Camellia nitidissima* Chi and *Hedyotis diffusa* based on the magnetic nanoparticles-PAMAM nano composites, in a successive step, high efficiency separation of the flavonoid substances can be realized by the technologies such as magnetic separation and microwave-assisted extraction.

DETAILED DESCRIPTION OF THE PREFERRED EMBODIMENTS

Figure 1:
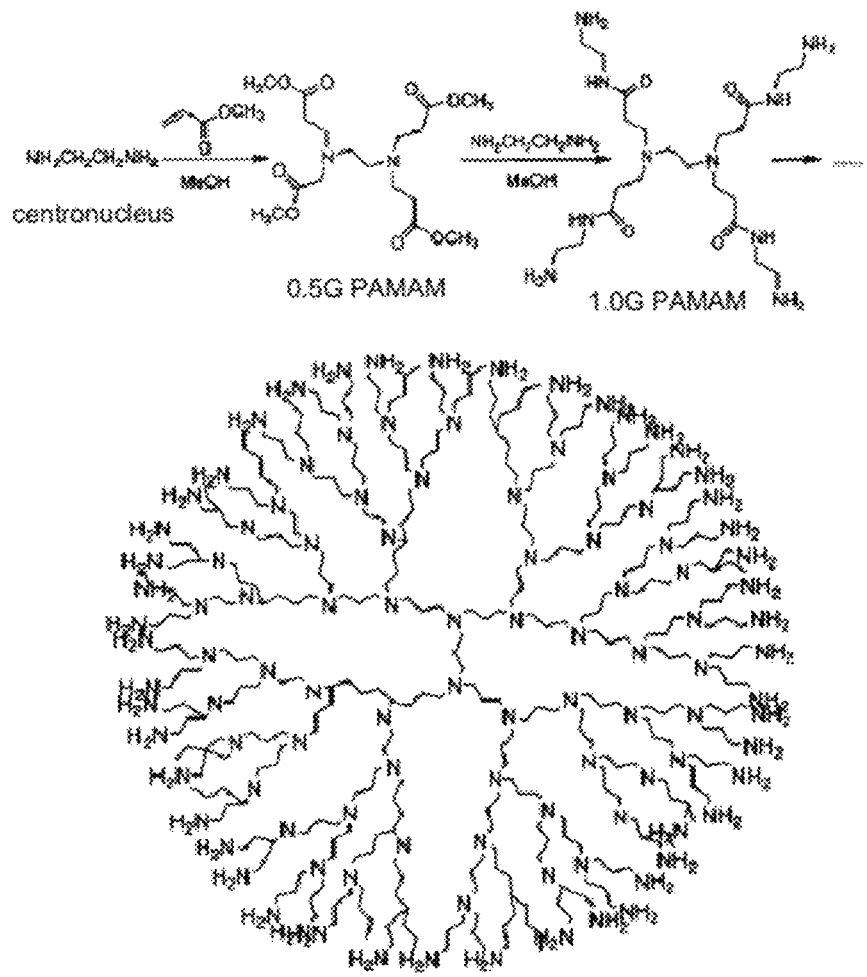
FIG. 1 is a classical synthetic route of PAMAM dendrimer.
Figure 2:
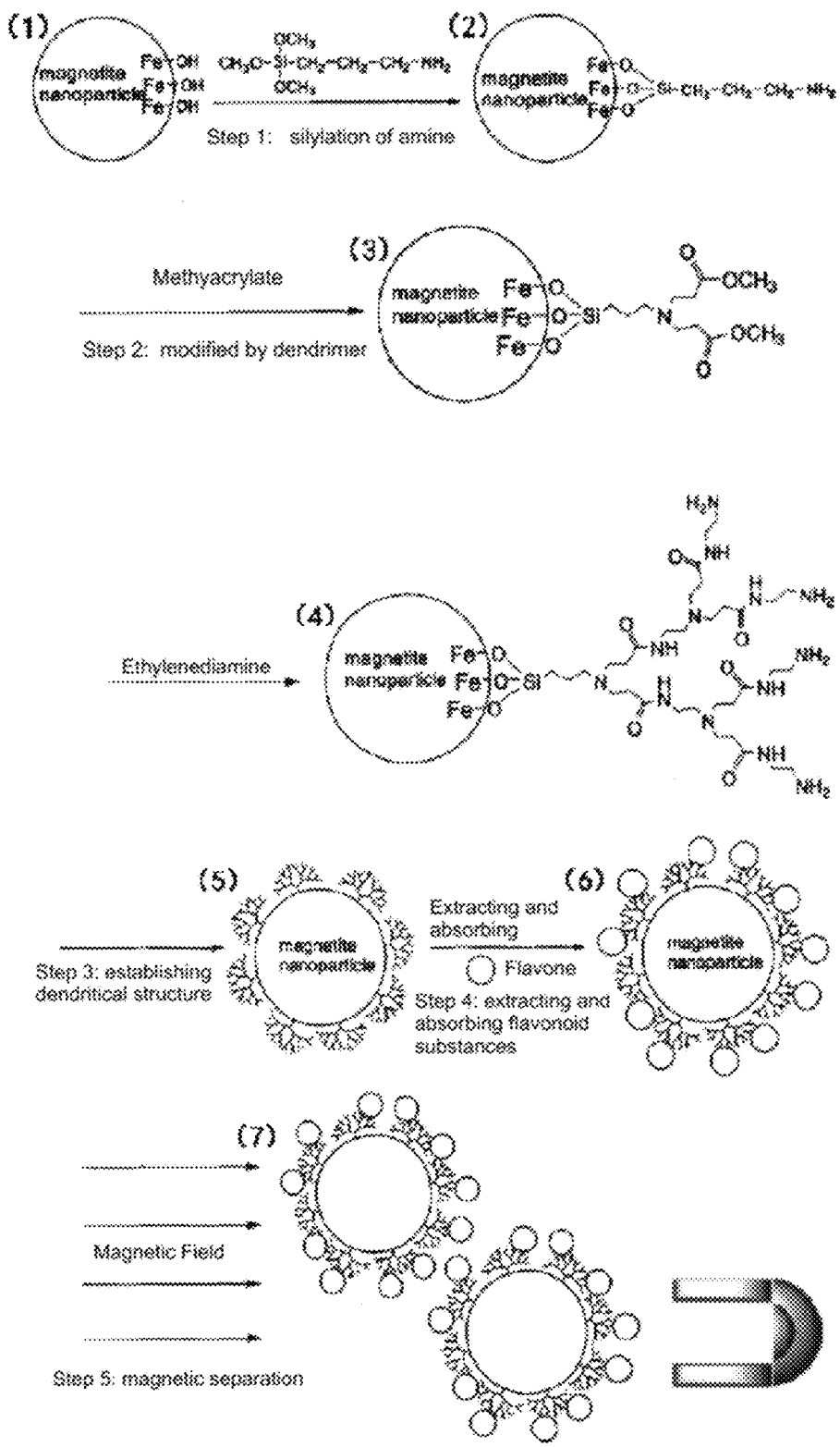
FIG. 2 shows a schematic diagram of $Fe_3O_4$ magnetic particle-PAMAM composites synthesis and flavonoid substances separation in *Camellia nitidissima* Chi and other plants.

The technical proposals of embodiments are described below dearly and completely with reference to the accompanying drawings. Obviously, it merely shows several specific embodiments of the present invention, rather than the whole embodiments. Other embodiments obtained by one of ordinary skilled in the art without creative work based on the embodiments of the present invention are all included within the protection scope of the present invention.

The flavonoid substances separation steps of the present invention are as follows, for better high efficient separation of the flavonoid substances adsorbed by PAMAM, the magnetic nanoparticles-PAMAM nano composites of the present invention is prepared by compounding PAMAM dendrimer and magnetic nanoparticles, like ferrites ($Fe_3O_4$, $\gamma$-$Fe_2O_3$ and $MeFe_2O_4$, wherein Me=Co, Ni, Mn), Fe, Co, Ni, alloy particles and iron nitrides (FeN, $Fe_2N$, $\epsilon$-$Fe_3N$ and $Fe_{16}N_2$) and other particles as well as generation 1.0-10.0 PAMAM dendrimer. Because the end of its ball structure is with rich $RNH_2$ functional group, and the middle part is with quantities of $R_2NH$, $R_3N$, quaternary ammonium and others, with faintly alkalinity and 10-30 grams solubility for every 100 grams of water, this kind of composites has strong adsorption effect on flavonoid substances with faintly acidity, which is good for the separation of flavonoid substances. The magnetic nanoparticles-PAMAM nano composites extracted and adsorbed with flavonoid substances with faintly acidity are separated from the extract through magnetic separation, and then the extracted and adsorbed flavonoid substances are separated with magnetic nanoparticles-PAMAM nano composites through solvent extraction technology.

Embodiment 1

Preparation of leaves of *Camellia nitidissima* Chi concentrate: picking fresh leaves of *Camellia nitidissima* Chi in spring; weighting it with electronic scale; performing screen for the picked fresh leaves of *Camellia nitidissima* Chi as per the standard of *Pharmacopoeia of China* (2010), smashing the optimized leaves of *Camellia nitidissima* Chi after washing; adding 50 L acetone (over 95%) into 20 kilograms of smashed leaves of *Camellia nitidissima* Chi and extracting for 5-6 h by Soxhlet extractor to obtain extract A; adding about 40 L acetone (over 95%) into extracted residue and performing ultrasonic wave processing for about 1.5 h under 40-60° C. to obtain extract B; mixing extract A and extract B and evaporating most acetone solvent by rotary evaporation of rotary evaporators, and finally obtaining about 2.0 L *Camellia nitidissima* Chi concentrate in organic phase.

Preparation process of $Fe_3O_4$ magnetic particles-4.0G PAMAM composites: preparing the mixture of 0.085 mol/L ferric chloride solution and 0.05 mol/L ferrous sulfate, then adding 1.5 mol/L ammonia solution into the mixture and stir vigorously until pH=9. Washing the obtained $Fe_3O_4$ magnetic nanoparticles for 5 times immediately and washing it with methanol for 3 times, the $Fe_3O_4$ magnetic nanoparticles is dispersed in methanol by magnetic separation, then the solution with 0.0128 mol/L concentration is obtained. Diluting the above prepared 25 mL methanol solution of $Fe_3O_4$ magnetic nanoparticles into 150 mL with methanol and performing ultrasonic processing for 30 min. Then adding 10 mL 3-aminopropyltriethoxysilane, the solution is stirred strongly together with ultrasonication for 7 h. After washing the obtained solution for 5 times with methanol, the magnetic separation is performed, the solution is dispersed in methanol to obtain 5 wt % solution for standby. 50 mL 5 wt % of magnetic nanoparticles methanol solution is used as the initial solution, adding 200 mL methanol solution with methyacrylate, performing ultrasonication to the mixture for 7 h in water bath at room temperature; then collecting magnetic nanoparticles by magnet and washing it for 5 times by methanol and performing magnetic separation; after washing, adding 40 mL methanol solution with ethylenediamine, performing ultrasound processing for 3 h at room temperature; then washing the magnetic nanoparticles for 5 times with methanol and performing magnetic separation; the methanol solution with methyacrylate and methanol solution with ethylenediamine are added repeatedly, the $Fe_3O_4$ magnetic nanoparticles modified by 4.0G dendrimer will be obtained after four times of cycles; washing the solution after cycle with 25 mL methanol for 3 times and with 25 mL water for 5 times, the $Fe_3O_4$ magnetic nanoparticles modified by 4.0G PAMAM dendrimer is collected and obtained by magnetic separation.

Extracting and separating flavonoid substances in *Camellia nitidissima* Chi: adding the obtained 10 g magnetic particles-4.0G PAMAM composites in the 2.0 L *Camellia nitidissima* Chi extract prepared in the first step, ultrasonic extracting 0.5 h under 400 W, after extraction, separating the $Fe_3O_4$-PAMAM nano composites adsorbed and extracted with flavonoid substances through magnetic separation, after separation, extracting the magnetic nanoparticles adsorbed with flavonoid substances several times with ethanol to extract the adsorbed flavonoid substances. Mixing the extract, removing ethanol by rotary evaporation and drying the anhydrous sodium sulfate for the night, then the flavonoid substances in *Camellia nitidissima* Chi will be obtained. Based on the detection method of total flavones in health food in *Inspection and Evaluation Technical Specification of Health Food* (2003), the content of flavonoid substances is more than 85% according to the separation and purification method of the present invention. The $Fe_3O_4$ magnetic particles-4.0G PAMAM magnetic nano composites can be recycled again after being washed by water and ethanol for several times, drying and activating.

Embodiment 2

Preparation of flowers of *Camellia nitidissima* Chi concentrate: picking fresh flowers of *Camellia nitidissima* Chi in autumn: weighting it with electronic scale; performing screen for the picked fresh flowers of *Camellia nitidissima* Chi as per the standard of *Pharmacopoeia of China* (2010), smashing the optimized leaves of *Camellia nitidissima* Chi after washing; adding 20-30 L acetone (over 95%) into 10 kilograms of smashed leaves of *Camellia nitidissima* Chi and extracting for 5-6 h by Soxhlet extractor to obtain extract A; adding about 20 L acetone (over 95%) into extracted residue and performing ultrasonication for about 1.5 h under 40-60° C. to obtain extract B; mixing extract A and extract B and evaporating most acetone solvent by rotary evaporation of rotary evaporators, and finally obtaining about 1.0 L *Camellia nitidissima* Chi concentrate in organic phase.

Preparation of $\gamma$-$Fe_2O_3$ magnetic particles-5.0G PAMAM composites: adding 2 mol/L sodium hydroxide solution in the 1 mol/L ferrous sulfate solution, then the white floc precipitation $Fe(OH)_2$ will be generated, and it becomes grayish green precipitation $Fe_6(SO_4)_2(OH)_4O_3$ rapidly. Dropping right amount of hydrogen peroxide into above solution with precipitation with dropper until it becomes from green to black. The above solution with precipitation is separated and precipitated by vacuum filter, then it is put into drying oven under 80° C. for an hour. The dried solution is calcined at 100-240° C. in muffle furnace to obtain $\gamma$-$Fe_2O_3$ red powder. The prepared magnetic nanoparticles are dispersed in the methanol to obtain the solution with 0.0128 mol/L concentration. Diluting the above prepared methanol solution of $\gamma$-$Fe_2O_3$ magnetic nanoparticles 25 mL into 150 mL with methanol and performing ultrasonic processing for 30 min. Then adding 10 mL 3-aminopropyltriethoxysilane, the solution is stirred strongly together with ultrasonication for 7 h. After washing the obtained solution for 5 times with methanol, the magnetic separation is performed, the solution is dispersed in methanol to obtain 5 wt % solution for standby. 50 mL 5 wt % of $\gamma$-$Fe_2O_3$ magnetic nanoparticles methanol solution is used as the initial solution, adding 200 mL methanol solution with methyacrylate, immersing the mixture into water bath at room temperature and performing ultrasonic processing for 7 h; then collecting magnetic nanoparticles by magnet and washing it for 5 times by methanol and performing magnetic separation; after washing, adding 40 mL methanol solution with ethylenediamine, performing ultrasonic processing for 3 h at room temperature, then washing the magnetic nanoparticles for 5 times by methanol and performing magnetic separation; the methanol solution with methyacrylate and methanol solution with ethylenediamine are added repeatedly, the magnetic nanoparticles modified by 5.0G dendrimer will be obtained after five times of cycles; washing the solution after cycle with 25 mL methanol for 3 times and with 25 mL water for 5 times, the $\gamma$-$Fe_2O_3$ magnetic nanoparticles modified by 5.0G PAMAM dendrimer is collected and obtained by magnetic separation.

Extracting and separating flavonoid substances in flowers of *Camellia nitidissima* Chi: adding the obtained $\gamma$-$Fe_2O_3$ magnetic particles-5.0G PAMAM composites in the 1.0 L *Camellia nitidissima* Chi flowers extract prepared in the first step, ultrasonic extracting 1 h under 400 W, after extraction, separating the $\gamma$-$Fe_2O_3$-5.0G PAMAM nano composites adsorbed and extracted with flavonoid substances through magnetic separation, after separation, extracting the $\gamma$-$Fe_2O_3$-5.0G PAMAM nano composites adsorbed with flavonoid substances several times with ethanol to extract the adsorbed flavonoid substances. Mixing the extract, removing methanol solvent by rotary evaporation and drying the anhydrous magnesium sulfate, then the flavonoid substances in *Camellia nitidissima* Chi will be obtained. Based on the detection method of total flavones in health food in Inspection and Evaluation Technical Specification of Health Food (2003), the content of flavonoid substances is more than 85% according to the separation and purification method for flavonoid substances in flowers of *Camellia nitidissima* Chi of the present invention. The $\gamma$-$Fe_2O_3$ magnetic particles-5.0G PAMAM composites can be recycled again after being washed several times, drying and activating.

Embodiment 3

Preparation of fruits of *Camellia nitidissima* Chi concentrate: picking fresh fruits of *Camellia nitidissima* Chi in November and December; weighting it with electronic scale; performing screen for the picked fruits of *Camellia nitidissima* Chi as per the standard of *Pharmacopoeia of China* (2010), smashing the optimized fruits of *Camellia nitidissima* Chi after washing, and vacuum drying at 50° C. to remove the moisture; adding 45 L ethanol (over 95%) into vacuum dried 15 kilograms fruits of *Camellia nitidissima* Chi and extracting for 5-6 h by Soxhlet extractor to obtain extract A; adding about 30 L ethanol (over 95%) into extracted residue and performing ultrasonication for about 1.5 h under 40-60° C. to obtain extract B; mixing extract A and extract B and evaporating most ethanol solvent by rotary evaporation of rotary evaporators, and finally obtaining about 1.5 L *Camellia nitidissima* Chi concentrate in organic phase.

Preparation of $Co_xNi_{1-x}Fe_2O_4$ nano Ni—Co ferrite magnetic particles-3.0G PAMAM composites: x means 0.1, 0.3, 0.5, 0.7, 0.9 etc. weighing the cobalt nitrate, nickel nitrate, ferric nitrate and citric acid by stoichiometric ratio, and utilizing distilled water to dissolve them into transparent color solution. The ammonia is dropped for the PH value of solution is between 7 and 8. The solution is heated in 90° C. water bath for 4-5 h to be sticky colloidal solution, and dried to drying gel at 120° C. The drying gel is heated in the muffle furnace from 120° C./h to 850° C./h, then after preserving the heat for 1 h, turning off the power supply for nature cooling. The prepared magnetic nanoparticles are ultrasonic dispersed in the methanol to obtain the solution with 0.0128 mol/L concentration. Diluting the above prepared methanol solution of $Co_xNi_{1-x}Fe_2O_4$ magnetic nanoparticles 25 mL into 150 mL with methanol and performing ultrasonic processing for 30 min. Then adding 10 mL 3-aminopropyltriethoxysilane, the solution is stirred strongly together with ultrasonication for 7 h. After washing the obtained solution for 5 times with methanol, the magnetic separation is performed, the solution is dispersed in methanol to obtain 5 wt % solution for standby. 50 mL 5 wt % $Co_xNi_{1-x}Fe_2O_4$ magnetic nanoparticles methanol solution is used as the initial solution, adding 200 mL methanol solution with methyacrylate, immersing the mixture into water bath at room temperature and performing ultrasonication for 7 h; then collecting magnetic nanoparticles by magnet and washing it for 5 times by methanol and performing magnetic separation; after washing, adding 40 mL methanol solution with ethylenediamine, performing ultrasonication for 3 h at room temperature; then washing the magnetic nanoparticles for 5 times with methanol and performing magnetic separation; the methanol solution with methyacrylate and methanol solution with ethylenediamine are added repeatedly, the magnetic nanoparticles modified by 3.0G dendrimer will be obtained after three times of cycles; washing the solution after cycle with 25 mL methanol for 3 times and with 25 mL water for 5 times, the $Co_xNi1-xFe2O4$ magnetic nanoparticles modified by 3.0G PAMAM dendrimer is collected and obtained by magnetic separation.

Extracting and separating flavonoid substances in fruits of *Camellia nitidissima* Chi: adding the obtained 7.5 g $Co_xNi_{1-x}Fe_2O_4$-3.0G magnetic particles-PAMAM composites (faintly alkalinity) in the 1.5 L *Camellia nitidissima* Chi fruits extract prepared in the first step, ultrasonic extracting 1.5 h under 400 W, after extraction, separating the $Co_xNi_{1-x}Fe_2O_4$-3.0G PAMAM nano composites adsorbed and extracted with flavonoid substances through magnetic separation, after separation, extracting the $Co_xNi_{1-x}Fe_2O_4$-3.0G PAMAM nano composites adsorbed with flavonoid substances (faintly acidity) several times with ethanol to extract the adsorbed flavonoid substances. Mixing the extract, removing ethanol solvent by rotary evaporation and drying the room empty sulfate, then the flavonoid substances in *Camellia nitidissima* Chi will be obtained. Based on the detection method of total flavones in health food in *Inspection and Evaluation Technical Specification of Health Food* (2003), the content of flavonoid substances is more than 85% according to the separation and purification method for flavonoid substances in flowers of the present invention. The $Co_xNi_{1-x}Fe_2O_4$-3.0G magnetic particles-3.0G PAMAM composites can be recycled again after being washed several times, drying and activating.

Embodiment 4

Preparation of leaves of *Camellia nitidissima* Chi concentrate: picking fresh leaves of *Camellia nitidissima* Chi in spring; weighting it with electronic scale; performing screen for the picked fresh leaves of *Camellia nitidissima* Chi as per the standard of *Pharmacopoeia of China* (2010), smashing the optimized leaves of *Camellia nitidissima* Chi after washing; adding 15 L methanol (over 95%) into 5 kilograms smashed leaves of *Camellia nitidissima* Chi and extracting for 5-6 h by Soxhlet extractor to obtain extract A; adding about 10 L methanol (over 95%) into extracted residue and performing ultrasonic processing for about 1.5 h under 40-60° C. to obtain extract B; mixing extract A and extract B and evaporating most methanol solvent by rotary evaporation of rotary evaporators, and finally obtaining about 0.5 L *Camellia nitidissima* Chi concentrate in organic phase.

Preparation process of $\gamma$-$Fe_4N$-6.0G PAMAM composites: preparing iron powder 10 g with 0.1 micron of particle size, the ammonia and hydrogen. Diluting the above prepared methanol solution of $\gamma$-$Fe_4N$ magnetic nanoparticles 25 mL into 150 mL with methanol and performing ultrasonication for 30 min. Then adding 10 mL 3-aminopropyltriethoxysilane, the solution is stirred strongly together with ultrasonication for 7 h. After washing the obtained solution for 5 times with methanol, the magnetic separation is performed, the solution is dispersed in methanol to obtain 5 wt % solution for standby. 50 mL 5 wt % of $\gamma$-$Fe_4N$ magnetic nanoparticles methanol solution is used as the initial solution, adding 200 mL methanol solution with methyacrylate, immersing the mixture into water bath at room temperature and performing ultrasonication for 7 h; then collecting magnetic nanoparticles by magnet and washing it for 5 times by methanol and performing magnetic separation; after washing, adding 40 mL methanol solution with ethylenediamine, performing ultrasonication for 3 h at room temperature; then washing the magnetic nanoparticles for 5 times with methanol and performing magnetic separation; the methanol solution with methyacrylate and methanol solution with ethylenediamine are added repeatedly, the $\gamma$-$Fe_4N$ magnetic nanoparticles modified by 6.0G dendrimer will be obtained after six times of cycles; washing the solution after cycle with 25 mL methanol for 3 times and with 25 mL water for 5 times, the $\gamma$-$Fe_4N$ magnetic nanoparticles modified by 6.0G PAMAM dendrimer is collected and obtained by magnetic separation.

Extracting and separating flavonoid substances in *Camellia nitidissima* Chi: adding the obtained $\gamma$-$Fe_4N$ magnetic particles-PAMAM composites (faintly alkalinity) in the 0.5 L *Camellia nitidissima* Chi leaves extract prepared in the first step, ultrasonic extracting 2 h under 400 W, after extraction, separating the $Fe_3O_4$-6.0G PAMAM nano composites adsorbed and extracted with flavonoid substances through magnetic separation, after separation, extracting the $Fe_3O_4$-6.0G PAMAM nano composites adsorbed with flavonoid substances several times by organic solvent. Mixing the extract, removing solvent by rotary evaporation and drying at room temperature, then the flavonoid substance in *Camellia nitidissima* Chi will be obtained. Based on the detection method of total flavones in health food in *Inspection and Evaluation Technical Specification of Health Food* (2003), the content of flavonoid substance is more than 85% according to the separation and purification method for flavonoid substances. The $Fe_3O_4$ magnetic particles-6.0G PAMAM composites can be recycled again after being washed several times, drying and activating.

Embodiment 5

Preparation of *Hedyotis diffusa* concentrate: picking fresh *Hedyotis diffusa* in autumn and removing root; weighting it with electronic scale; performing screen for the picked fresh *Hedyotis diffusa* as per the standard of *Pharmacopoeia of China* (2010), smashing the optimized *Hedyotis diffusa* after washing; adding over 95% acetone into 20 kilograms of smashed *Hedyotis diffusa* and extracting for 5-6 h by Soxhlet extractor to obtain extract A; adding over 95% acetone into extracted residue and performing ultrasonic processing for about 1.5 h under 40-60° C. to obtain extract B; mixing extract A and extract B and evaporating most acetone solvent by rotary evaporation of rotary evaporators, and finally obtaining about 2.0 L *Hedyotis diffusa* concentrate in organic phase.

Preparation processes of $Fe_3O_4$ magnetic particles-4.0G PAMAM composites: preparing the mixture of 0.085 mol/L ferric chloride solution and 0.05 mol/L ferrous sulfate, then adding 1.5 mol/L ammonia solution into the mixture and stir vigorously until pH=9. Washing the obtained $Fe_3O_4$ magnetic nanoparticles for 5 times immediately and washing it by methanol for 3 times, the $Fe_3O_4$ magnetic nanoparticles is dispersed in methanol by magnetic separation, then the solution with 0.0128 mol/L concentration is obtained. Diluting the above prepared methanol solution of $Fe_3O_4$ magnetic nanoparticles 25 mL into 150 mL with methanol and performing ultrasonic processing for 30 min. Then adding 10 mL 3-aminopropyltriethoxysilane, the solution is stirred strongly together with ultrasonication for 7 h. After washing the obtained solution for 5 times with methanol, the magnetic separation is performed, the solution is dispersed in methanol to obtain 5 wt % solution for standby. 50 mL 5 wt % $Fe_3O_4$ magnetic nanoparticles methanol solution is used as the initial solution, adding 200 mL methanol solution with methyacrylate, immersing the mixture into water bath at room temperature and performing ultrasonication for 7 h; then collecting magnetic nanoparticles by magnet and washing it for 5 times by methanol and performing magnetic separation; after washing, adding 40 mL methanol solution with ethylenediamine, performing ultrasonication for 3 h at room temperature; then washing the magnetic nanoparticles for 5 times with methanol and performing magnetic separation; the methanol solution with methyacrylate and methanol solution with ethylenediamine are added repeatedly, the $Fe_3O_4$ magnetic nanoparticles modified by 4.0G dendrimer will be obtained after four times of cycles; washing the solution after cycle with 25 mL methanol for 3 times and with 25 mL water for 5 times, the $Fe_3O_4$ magnetic nanoparticles modified by 4.0G PAMAM dendrimer is collected and obtained by magnetic separation.

Extracting and separating flavonoid substances in *Hedyotis diffusa*: adding the obtained $Fe_3O_4$ magnetic particles-4.0G PAMAM composites (faintly alkalinity) in the 2.0 L *Camellia nitidissima* Chi extract prepared in the first step, ultrasonic extracting 0.5 h under 400 W, after extraction, separating the $Fe_3O_4$-PAMAM nano composites adsorbed and extracted with flavonoid substances (faintly acidity) through magnetic separation, after the completion of $Fe_3O_4$-PAMAM separation, extracting the magnetic nanoparticles adsorbed with flavonoid substances several times with ethanol to extract the adsorbed flavonoid substances. Mixing the extract, removing ethanol by rotary evaporation and drying the anhydrous sodium sulfate for the night, then the flavonoid substances in *Hedyotis diffuse* will be obtained. Based on the detection method of total flavones in health food in *Inspection and Evaluation Technical Specification of Health Food* (2003), the content of flavonoid substance is more than 85% according to the separation and purification method of the present invention. The $Fe_3O_4$ magnetic particles-4.0G PAMAM magnetic nano composites can be recycled again after being washed by water and ethanol for several times, drying and activating.

Embodiment 6

Preparation of leaves of *Rhus chinensis* concentrate: picking fresh leaves of *Rhus chinensis* weighting it with electronic scale; performing screen for the picked fresh leaves of *Rhus chinensis* as per the standard of *Pharmacopoeia of China* (2010), smashing the optimized leaves of *Rhus chinensis* after washing; adding 20-30 L ethanol (over 95%) into 10 kilograms smashed leaves of *Rhus chinensis* and extracting for 5-6 h by Soxhlet extractor to obtain extract A; adding about 20 L ethanol (over 95%) into extracted residue and performing ultrasonic processing for about 1.5 h under 40-60° C. to obtain extract B; mixing extract A and extract B and evaporating most ethanol solvent by rotary evaporation of rotary evaporators, and finally obtaining about 1.0 L leaves of *Rhus chinensis* concentrate in organic phase.

Preparation of $\gamma$-$Fe_2O_3$ magnetic particles-5.0G PAMAM composites: adding 2 mol/L sodium hydroxide solution in the 1 mol/L ferrous sulfate solution, then the white floc precipitation $Fe(OH)_2$ will be generated, and it becomes grayish green precipitation $Fe_6(SO_4)_2(OH)_4O_3$ rapidly. Dropping right amount of hydrogen peroxide into above solution with precipitation with dropper until it becomes from green to black. The above solution with precipitation is separated and precipitated by vacuum filter, and then it is put into drying oven under 80° C. for an hour. The dried solution is calcined at 100-240° C. in muffle furnace to obtain $\gamma$-$Fe_2O_3$ red powder. The prepared magnetic nanoparticles are dispersed in the methanol to obtain the solution with 0.0128 mol/L concentration. Diluting the above prepared methanol solution of $\gamma$-$Fe_2O_3$ magnetic nanoparticles 25MI into 150 mL with methanol and performing ultrasonic processing for 30 min. Then adding 10 mL 3-aminopropyltriethoxysilane, the solution is stirred strongly together with ultrasonication for 7 h. After washing the obtained solution for 5 times with methanol, the magnetic separation is performed, the solution is dispersed in methanol to obtain 5 wt % solution for standby. 50 mL 5 wt % of $\gamma$-$Fe_2O_3$ magnetic nanoparticles methanol solution is used as the initial solution, adding 200 mL methanol solution with methyacrylate, immersing the mixture into water bath at room temperature and performing ultrasonication for 7 h; then collecting magnetic nanoparticles by magnet and washing it for 5 times by methanol and performing magnetic separation; after washing, adding 40 mL methanol solution with ethylenediamine, performing ultrasonication for 3 h room temperature; then washing the magnetic nanoparticles for 5 times with methanol and performing magnetic separation; the methanol solution with methyacrylate and methanol solution with ethylenediamine are added repeatedly, the magnetic nanoparticles modified by 5.0G dendrimer will be obtained after five times of cycles; washing the solution after cycle with 25 mL methanol for 3 times and with 25 mL water for 5 times, the $\gamma$-$Fe_2O_3$ magnetic nanoparticles modified by 5.0G PAMAM dendrimer is collected and obtained by magnetic separation.

Extracting and separating flavonoid substances in flowers of *Rhus chinensis*: adding the obtained $\gamma$-$Fe_2O_3$ magnetic particles-5.0G PAMAM composites (faintly alkalinity) in the 1.0 L *Camellia nitidissima* Chi flowers extract prepared in the first step, ultrasonic extracting 1 h under 400 W, after extraction, separating the $\gamma$-$Fe_2O_3$-5.0G PAMAM nano composites adsorbed and extracted with flavonoid substances through magnetic separation, after separation, extracting the $\gamma$-$Fe_2O_3$-5.0G PAMAM nano composites adsorbed with flavonoid substances several times with ethanol to extract the adsorbed flavonoid substance. Mixing the extract, removing methanol solvent by rotary evaporation and drying the anhydrous magnesium sulfate, then the flavonoid substances in *Rhus chinensis* will be obtained. Based on the detection method of total flavones in health food in *Inspection and Evaluation Technical Specification of Health Food* (2003), the content of flavonoid substances is more than 85% according to the separation and purification method of flavonoid substances in flowers of *Camellia nitidissima* Chi of the present invention. The $\gamma$-$Fe_2O_3$ magnetic particles-5.0G PAMAM composites can be recycled again after being washed several times, drying and activating.

The technology of the present invention also applies to other leaves, flowers, fruits and roots of plants enriched in flavonoid substances, such as tea, *Chrysanthemum indicum*, *Ginkgo biloba*, mulberry leaf, *Artemsia argyi*, honeysuckle, grapefruit, orange, soybean, ginger, star anise, celery, pineapple, guava, corn stigma, *Patrinia scaniosaefolia*, clover, *Houttuynia cordata* thunb, licorice, *Rhus chinensis*, *Phyllanthus ruinaria*, Cactus, *Selaginella tamariscina*, *Hedyotis diffuse*, Burdock, *Mahonia bealei*, *Pteris semipinnata*, *Apocynum venetum*, *Lespedeza dunnii*, *Cynomorium songaricum rupr*, *Sarcandra glabra* etc., the extraction and separation method for flavonoid substances in above plants is similar with the magnetic particles-PAMAM nano magnetic separation technology.

It is obvious that the present invention is not limited to above embodiments for those skilled in the art, and the present invention can be realized by other embodiments without departing from the spirit or basic feature of the present invention. So the embodiments are demonstrative and non-restrictive, it is intended that the invention be limited only in terms of the appended claims, rather than above embodiments. So any variations that equivalent to the content and scope of claims shall fall into the protection scope of the present invention.

Besides, while the specification has described embodiments, it should be understood that not each embodiment merely include one independent technical proposal, it is for clearly description, the skilled in the art shall regard the specification as a whole, the technical proposals of each embodiments can be combined to form other embodiments.

I claim:

1. A method for separating flavonoid substances in *Camellia nitidissima* Chi based on magnetic nanoparticle-PAMAM nano composites, comprising:
preparing PAMAM dendrimer:
performing Michael addition reaction between ethylenediamine and methyacrylate to obtain generation 0.5 polyamidoamine dendrimer, namely PAMAM G0.5; wherein the Michael addition reaction is performed under 25° C.;
reacting the obtained PAMAM G0.5 with excessive ethylenediamine under 25° C. to obtain generation 1.0 polyamidoamine dendrimer, namely PAMAM G1.0;
repeating the above two steps to obtain PAMAM with different generation;
preparing magnetic nanoparticle-PAMAM nano composites
dispersing magnetic nanoparticles into methanol through magnetic separation to obtain methanol solution with 0.0128 mol/L concentration;
diluting 25 mL methanol solution containing magnetic nanoparticles therein to 150 mL by methanol and performing ultrasonication for 30 min;
adding 10 mL 3-aminopropyltriethoxysilane, stirring and performing ultrasonication for 7 hours; performing magnetic separation on the obtained solution after washing it by methanol for 5 times; dispersing the washed solution in methanol to obtain 5 wt % magnetic nanoparticle methanol solution;
adding 200 mL methanol solution with methyacrylate into 50 mL 5 wt % magnetic nanoparticle methanol solution to obtain a mixed solution, wherein a volume concentration of the methyacrylate is 20%;
performing ultrasonication to the mixed solution for 7 hrs in water bath at room temperature;
collecting magnetic nanoparticles by magnet and washing it for 5 times by methanol and performing magnetic separation;
adding 40 mL methanol solution with ethylenediamine, the volume concentration of the ethylenediamine is 20%, performing ultrasonication for 3 hrs at room temperature;
washing the magnetic nanoparticles for 5 times with methanol and performing magnetic separation; repeatedly adding the methanol solution with methyacrylate and methanol solution with ethylenediamine; obtaining higher generations of magnetic nanoparticles modified by dendrimer for each cycle;
washing the solution after cycle with 25 mL methanol for 3 times and washing with 25 mL water for 5 times; and obtaining the magnetic nanoparticles modified by PAMAM dendrimer by magnetic separation; and
extracting and performing magnetic separation on the flavonoid substances in *Camellia nitidissima* Chi:
adding the obtained magnetic nanoparticle-PAMAM nano composites in a *Camellia nitidissima* Chi extract;
extracting for 0.5-3 hrs under ultrasound or microwave condition;
separating the nanoparticle-PAMAM nano composites adsorbed and extracted with flavonoid substances through magnetic separation after the extraction, the flavonoid substances adsorbed by magnetic nanoparticles are extracted and separated by using an organic solvent from separated nanoparticle-PAMAM nano composites.

2. The method of claim 1, wherein the magnetic nanoparticles are $Fe_3O_4$.

3. The method of claim 1, wherein the organic solvent is methanol.

* * * * *